United States Patent
Machado et al.

(10) Patent No.: US 7,866,883 B2
(45) Date of Patent: Jan. 11, 2011

(54) RADIOGRAPHIC FILM POSITIONING DEVICE AND A PROCESS FOR OBTAINING RADIOGRAPHIC IMAGES

(76) Inventors: Asbel Rodrigues Machado, Rua Tapajós, 1000, Apto 101, Saraiva, 38408-414 Uberlândia MG (BR); Eder Ferreira Rangel, Rua Bernardo Guimarães 577, Apto 602, Bairro Fundinho, 38400-198—Uberlândia, MG (BR); Keuler Ferreira Rangel, Rua Jornalista João de Oliveira, 1180, Apto 801, Santa Mônica, 38408-248 Uberlândia MG (BR)

( * ) Notice: Subject to any disclaimer, the term of this patent is extended or adjusted under 35 U.S.C. 154(b) by 82 days.

(21) Appl. No.: 12/365,491

(22) Filed: Feb. 4, 2009

(65) Prior Publication Data

US 2010/0195790 A1    Aug. 5, 2010

(51) Int. Cl.
A61B 6/14    (2006.01)
(52) U.S. Cl. .................. 378/170; 378/168; 378/191
(58) Field of Classification Search .......... 378/168, 378/169, 170, 191
See application file for complete search history.

(56) References Cited

U.S. PATENT DOCUMENTS

| | | | | |
|---|---|---|---|---|
| 4,251,732 A | * | 2/1981 | Fried | 378/170 |
| 4,295,050 A | * | 10/1981 | Linden | 378/205 |
| 4,731,808 A | * | 3/1988 | Ogunsunlade | 378/170 |
| 5,090,047 A | * | 2/1992 | Angotti et al. | 378/170 |
| 5,119,410 A | * | 6/1992 | Donato | 378/170 |
| 5,473,662 A | * | 12/1995 | Barish | 378/170 |
| 5,625,666 A | * | 4/1997 | Willis | 378/167 |
| 5,737,388 A | * | 4/1998 | Kossila | 378/168 |
| 5,799,058 A | * | 8/1998 | Willis et al. | 378/168 |
| 6,033,111 A | * | 3/2000 | Winters et al. | 378/170 |
| 6,102,566 A | * | 8/2000 | Willis | 378/170 |
| 7,661,880 B2 | * | 2/2010 | Calderwood et al. | 378/170 |

FOREIGN PATENT DOCUMENTS

| | | |
|---|---|---|
| BR | 6400302 U | 5/1984 |
| BR | 7401153 U | 3/1996 |
| BR | 8300979 U | 3/2005 |
| BR | 8301363 U | 4/2005 |

OTHER PUBLICATIONS

The English translation of Brazilian Patent Application entitled "A Reference Support for a Dental Implant, a Radiographic and/or Tomographic Reference Support Mounting-Frame and a Prosthetic-Crown Sounding Guide,".

* cited by examiner

Primary Examiner—Allen C. Ho
(74) Attorney, Agent, or Firm—Alston & Bird LLP

(57) ABSTRACT

One describes a radiographic film positioning device, particularly de-signed for use in dentistry, provided with a first assembly for positioning at least one radiographic film that comprises at least one association means for association with a radiographic support, positionable substantially perpendicular to a bone portion of the patient.

15 Claims, 3 Drawing Sheets

Figure 1:
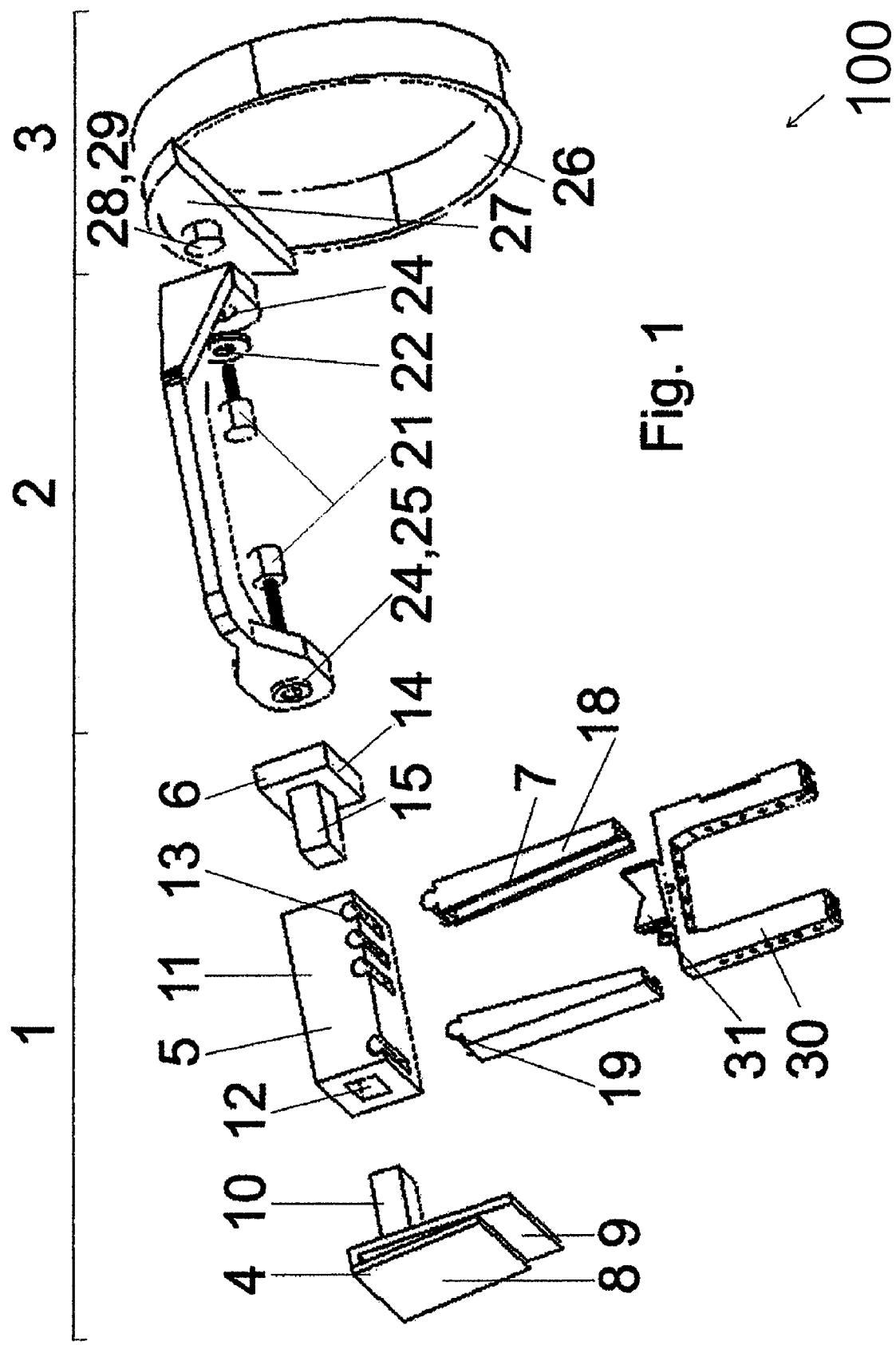

RADIOGRAPHIC FILM POSITIONING DEVICE AND A PROCESS FOR OBTAINING RADIOGRAPHIC IMAGES

The present invention relates to a radiographic film positioning device, particularly, but not compulsorily designed for use in dentistry, which guarantees correct positioning of the film with respect to the alveolar bones of the patient's mouth and, as a result, enables one to obtain precise true radiographic images, without deformations resulting from wrong alignment of the film with respect to the bone.

The present invention has the objective of providing a radiographic film positioning device that enables rigid fixation thereof with a radiographic support, so that the radiographic image produced can be perfectly correlated in space with the contour of the bone relief obtained with a transgingival probing carried out with said support, thus enabling one to determine the ideal values of the position and of the angle of a dental implant which is to be installed in the region being X-rayed.

The accuracy of the radiographic images obtained makes the present positioning device extremely suitable for the planning of the positioning of dental implants.

The present invention further relates to a process for obtaining radiographic images (preferably, but not compulsorily designed for obtaining periapical radiographic images), wherein such images do not exhibit deformations and/or distortions resulting from wrong alignment of the film with respect to the bone. For this purpose, the present process guarantees, by means of the present positioning device, parallelism between the radiographic film and the border of the alveolar bone of the patient.

DESCRIPTION OF THE PRIOR ART

In order to make radiographic images, a film of a suitable material (popularly referred to as "plate" (for "radiograph")) should be positioned adjacent the portion of the patient's body, the image of which is to be obtained. After positioning the plate, one subjects the region to application of X-rays, which upon being emitted go through the patient's body and, finally, reaches the plate.

When the X-rays reach the plate, they expose it, which after a development process enables reconstitution of the image, which in turn enables identification of bones and tissues inside the patient's body.

In order to obtain radiographs of segments of the dental arcade of a patient by the parallelism technique, it is necessary to use supports or devices that enable one to position the film correctly inside the patient's mouth, so that the X-rays emitted by the equipment will pass through the teeth and the upper-jaw bone or lower-jaw bone (the upper and lower bones of the mouth, respectively) and expose the film, enabling the obtainment of the respective image after development. These supports are usually known as radiographic film positioning devices or radiographic positioners.

The radiographic positioners used at present enable the positioning of the film inside the patient's mouth, but do not guarantee parallelism between the film and the border of the patient's alveolar bone. As a result, the images obtained almost invariably exhibit deformations/distortions due to wrong alignment of the film with respect to the bone, and to not exhibit geometrical and dimensional fidelity.

If, for example, for detecting tooth-decays geometrical and dimensional fidelity is not imperious, for other dental procedures like carrying out implants, this information becomes more important, for the reasons commented on hereinafter.

Specifically, the procedure of applying a dental implant is a surgical procedure that requires a number of process steps, so that the implant will be correctly and steadily positioned in place.

A dental implant is an element fixed to the bone portion of the patient's maxilla or mandible, which enables one to fix a prosthesis crown (a "synthetic tooth") at the place where the natural tooth was originally positioned.

For correct fixation of the implant, it is necessary to perforate the bone portion at the site that is most suitable for this purpose, positioning the implant there, which rapidly interacts with the bone tissue and becomes correctly fixed (osseointegration).

The procedure of perforating the bone portion of the patient should be carefully studied, since making the perforation at an inadequate site may impair the result of the implantation, in both the esthetic and sometimes the functional aspects, if the fixation becomes difficult due to the incorrect position of the orifice.

In the case of an implant applied to the lower alveolar bone (mandible), there is the aggravating factor of the presence of nerve tissue (lower alveolar nerve) in an inner cavity that goes through the bone, for which reason this situation needs to be considered unfailingly at the time of carrying out the implantation procedure. If the nerve is reached and damaged, this may result in partial paralysis of the patient's face, becoming permanent sequelae in most cases.

In case the implant is carried out on the upper alveolar bone (maxilla), there is no important nerve end, but on the other hand right above are the maxillary sinus and the nasal cavity floor, which may not be perforated at the risk of the patients undergoing severe hemorrhage and/or infection (sinusitis). When said parts are perforated, it generally becomes necessary to position the implant at another orifice. However, if the first orifice was already correctly positioned, then the final orifice of the implant may be impaired.

Therefore, the study of the correct site for making the orifice must take into consideration numberless variable, such as the bone makeup of the patient, shape and positioning of the implant, possible loss of bone due to the inadequate oral hygiene, location of the lower alveolar nerve, maxillary sinus and nasal cavity floor, among others.

In order to carry out this study, the professional makes use of clinical examinations and of image, such as computerized-tomography (TC) and radiographic images, which provide an effective view of the bone makeup of the patient's face.

In the case of using radiographic imaging, the images must be true and may not exhibit distortions or deformations, on pain of impairing the definition of the correct site for positioning the implant. And, since radiography produces a two-dimensional (height and width) image, which does not enable one to view the third dimension, that is to say, the thickness of the bone border, the professional resorts to a gingival probing examination.

The gingival probing, as a rule, is carried out from successive perforations in the gum at the desired site, which enables one to map the cross-section of the bone (thickness). In possession of the values of the gum depth at each site, the professional manages to draw an estimated outline of the bone located below it.

In possession of the radiographic images and of the data obtained after making the proving, the professional can calculate the ideal positioning of the implant with respect to its horizontal positioning and angle.

However, the efficiency of all this procedure is impaired because, in spite of the result of the gingival probing, irreparable distortions or deformations of the radiographic images still exist, which are due to limitations in the present radiographic positioners, which are not able to guarantee parallelism between the radiographic film and the border of the patient's alveolar bone, unless by a stoke of luck.

A first radiographic film positioning device is disclosed in the Brazilian patent case BRMU 6400302-7, and is constituted by a support that maintains a radiographic plate in the desired position inside the mouth. The support is integral with a shaft, which in turn goes through a fastener that fastens the whole assembly to the X-ray cannon, the supports, shafts and fasteners being of varying shapes in order to embrace all and every type of dental formation encountered.

According to that document, the device is designed for use at dentist's offices or clinics, together with the radiography cannon, and is aimed at facilitating the operation and positioning X-ray pictures made from any angle or depth of the patient's mouth.

As serious drawbacks, the device disclosed ion document BRMU 6400302-7 does not provide rigid fixation and does not guarantee, with sufficient precision, perfect positioning and parallelism of the film with the object being X-rayed. Such failure results from the fact that fixation in a given position is guaranteed by occlusion, so that, when the patients bites, displacement and inclination of the positioner may occur (and usually occurs), depending on the anatomy of the teeth and on the intensity of the bite.

Brazilian patent BRMU 8300979-5 relates to a device for positioning an individualized film for each patient, constituted of a circular bracket, the opening and closing of which are effected by means of two shoes that are adjustable by screws and threads, to which the radiographic cylinder of common radiography apparatus is coupled, fastened to the opposite side of the shoes, where the radiological positioner is located.

The positioner comprises a metallic shaft having two perpendicular folds, with to pins at one end for coupling with respective to orifices provided in the individualized film device, which in turn has a body provided with upper and lower flaps, having at its adjacent end a wedge-shaped support, where the radiographic film is placed.

In order to operate the invention, the dental surgeon applied dental resin to the upper and lower flaps of the individualized film device and promotes the rigid engagement of the patient's teeth with it, forming a mark of the upper and lower teeth, which will be stored for future use in taking the post-treatment X-ray picture.

The device disclosed in that document, in spite of presenting rigid fixation by means of the resin, does not provide means for guaranteeing parallelism, because the resin only fixes the device in the position in which it is, nor does it teach means for guaranteeing that this positioning is correct, keeping the radiographic film parallel to the bone.

As another drawback, this is a quite toilsome procedure, since the making of the bite guide with resin is always individualized, specifically intended only for that patient, which requires more time and makes the process expensive.

The only efficient use of this device is that in which one needs to take the X-ray picture again at the end of the treatment of a patient, keeping exactly the same position in which it was made in the beginning of the treatment.

Brazilian document BRMU 8301363-6 relates to an auxiliary positioner for a method of radiographic location, constituted by three versions (a version that serves for the left region, another for the right region and the last one for the front region of the mandible and maxilla).

The positioner has, in its versions, a C-shaped horizontal bar articulated leftwards and rightwards and an L-shaped one articulated to the front, at its end a support for radiographic films, which has referential retractile motion through a lower guide which the professional can adjust according to examination need (the indications are marked in high relief, two of them on the support and one on the horizontal bar).

At the upper flap, a foam-protection is further provided, in order not to injure the patient's mouth, and in the back region there is a serration for better anchorage on the teeth.

Finally, fixed to the horizontal bar there are three locating rings intentionally coupled to the new positioner in precise location, which are applied to the radiographic cylinder of ordinary radiography apparatus.

Although this device is adjustable, it is quite different from the object of the present invention and is not applied in planning implant surgery (it is specific for locating technique=Clark method).

Finally, Brazilian document BRMU 7401153-7 relates to a device for making periapical radiography, which aids in performing techniques of making periapical radiographs used in dentistry, mainly in the field of practical endodontics, consisting of special auxiliary nippers, auxiliary plate (children's and adult's models, respectively) and rubber or silicone adapter.

This device is specific for application in endodontical treatment and is not effective for making radiographic shots with a view to making implants, because, since it does not have rigid fixation, it cannot guarantee with sufficient accuracy the perfect positioning and parallelism of the film with the object being X-rayed (bone). This failure results from the fact that the fixation in a given position is guaranteed by occlusion, so that, when the patient bites, displacement and inclination of the positioner may occur depending on the anatomy of the teeth and on the intensity of the bite.

Until now, one had not developed any radiographic film positioning device, mainly for making periapical radiographic images, which could enable and guarantee great accuracy in the parallelism between radiographic film and the border of the patient's alveolar bone, thus guaranteeing the obtainment of periapical radiographic images without deformation/distortion due to wrong alignment of the film with respect to the bone.

So far, no radiographic film positioning device had been developed, mainly for performing periapical radiographic imaging, which could provide rigid fixation of the radiographic positioner with a radiographic support, so that the radiographic image produced could be perfectly correlated in space with the contour of the bone relief obtained by means of a transgingival probing carried out through said support, and that could enable the obtainment of the ideal values of the position and of the angle of a dental implant that is to be installed in the region being X-rayed.

So far, no process for obtaining radiographic images (preferably, but not compulsorily designed for obtaining periapical radiographic images) had been developed, without such images presenting deformations/distortions due to wrong alignment of the film with respect to the bone.

OBJECTIVES OF THE INVENTION

An objective of the present invention is to provide a radiographic film positioning device, mainly for performing periapical radiographic images, which enables and guarantees great accuracy in parallelism between the radiographic film and the border of the alveolar bone of the patient, thus guaranteeing the obtainment of radiographic images without deformations/distortions due to wrong alignment of the film with respect to the bone.

Another objective of the present invention is to provide a radiographic film positioning device that, besides guaranteeing great accuracy in parallelism between the radiographic film and the border of the alveolar bone of the patient, is easy and simple to use, so as to encourage the employ thereof by dentists.

A further objective of the present invention is to provide a process for obtaining radiographic images (preferably, but not compulsorily designed for obtaining periapical radiographic images), without such images presenting deformations/distortions due to wrong alignment of the film with respect to the bone.

The present invention has also the additional objective of providing a process for obtaining radiographic images, which provides means for calculating the degree of magnification of the image, enabling the value of magnification found to be compensated for in the initially obtained dimensions in the radiographic image, for the purpose of planning a dental implant.

Finally, a further objective of the present invention is to provide a process for obtaining radiographic images that provides rigid fixation of the positioner with a radiographic support, so that the image obtained can be perfectly correlated in space with the result of a transgingival probing.

BRIEF DESCRIPTION OF THE INVENTION

The objectives of the present invention are achieved by means of a radiographic film positioning device, particularly designed for use in dentistry, provided with a first assembly for positioning at least one radiographic film that comprises at least one means for association to a radiographic support that is positioned substantially perpendicular to a bone portion of the patient.

Also, the objectives of the present invention are achieved by means of a radiographic film positioning device, particularly designed for use in dentistry, provided with a first assembly comprising at least one means for association to a radiographic support and a film support element, the support element being substantially perpendicular to the radiographic support.

Further, the objectives of the present invention are achieved by means of a process for obtaining radiographic images, by positioning at least one positioning device having a first assembly for positioning at least one radiographic film that comprises at least one means for association to a radiographic support, as defined above, in the dental arcade of a patient, the process comprising the following steps:

(i): mounting the device;

(ii): positioning the device with respect to the dental arcade;

(iii): positioning at least one X-ray emitting source with respect to the device; and (iv): actuating the X-ray emitting source.

BRIEF DESCRIPTION OF THE DESIGNS

Figure 2:
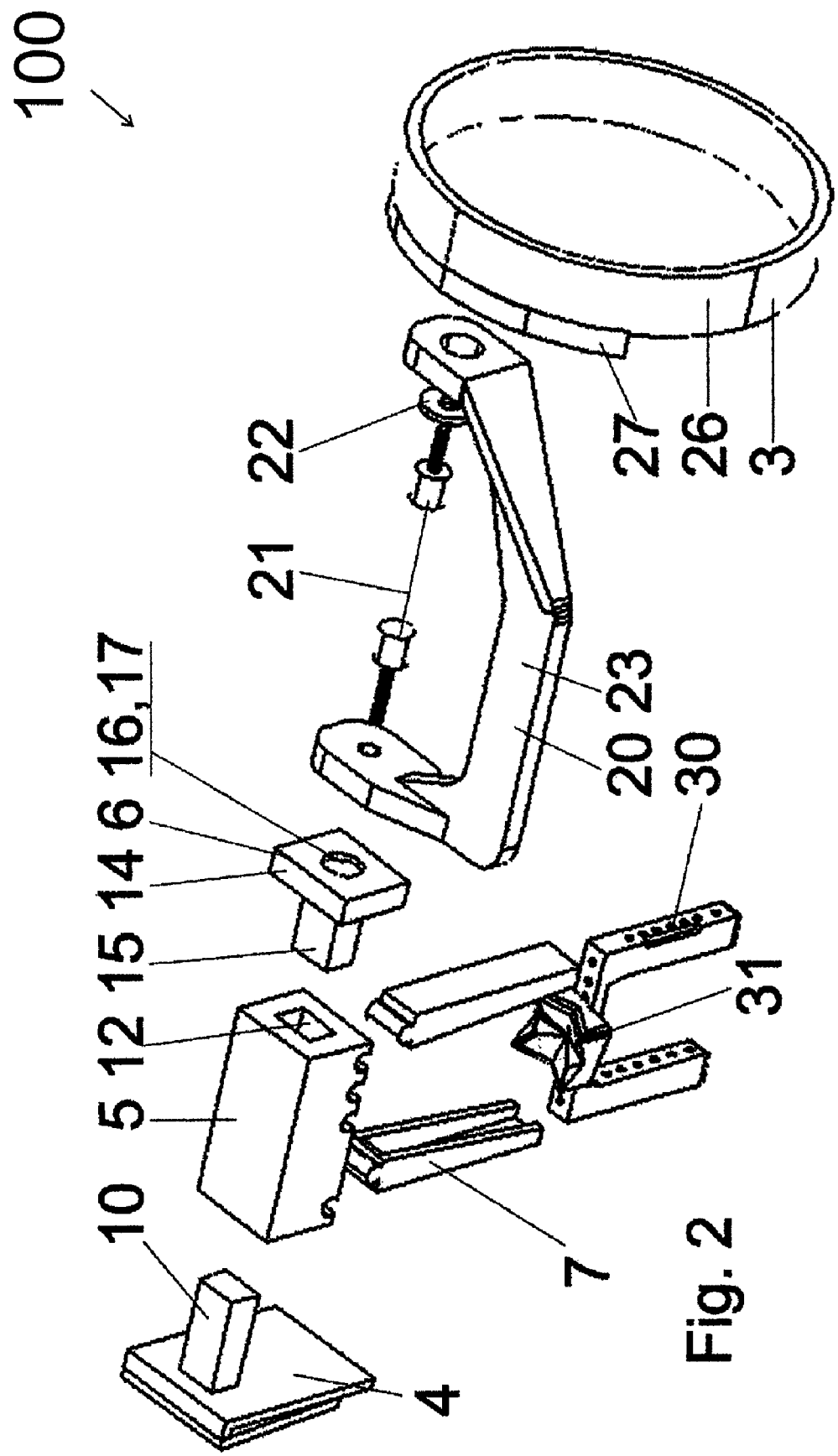
Figure 3:
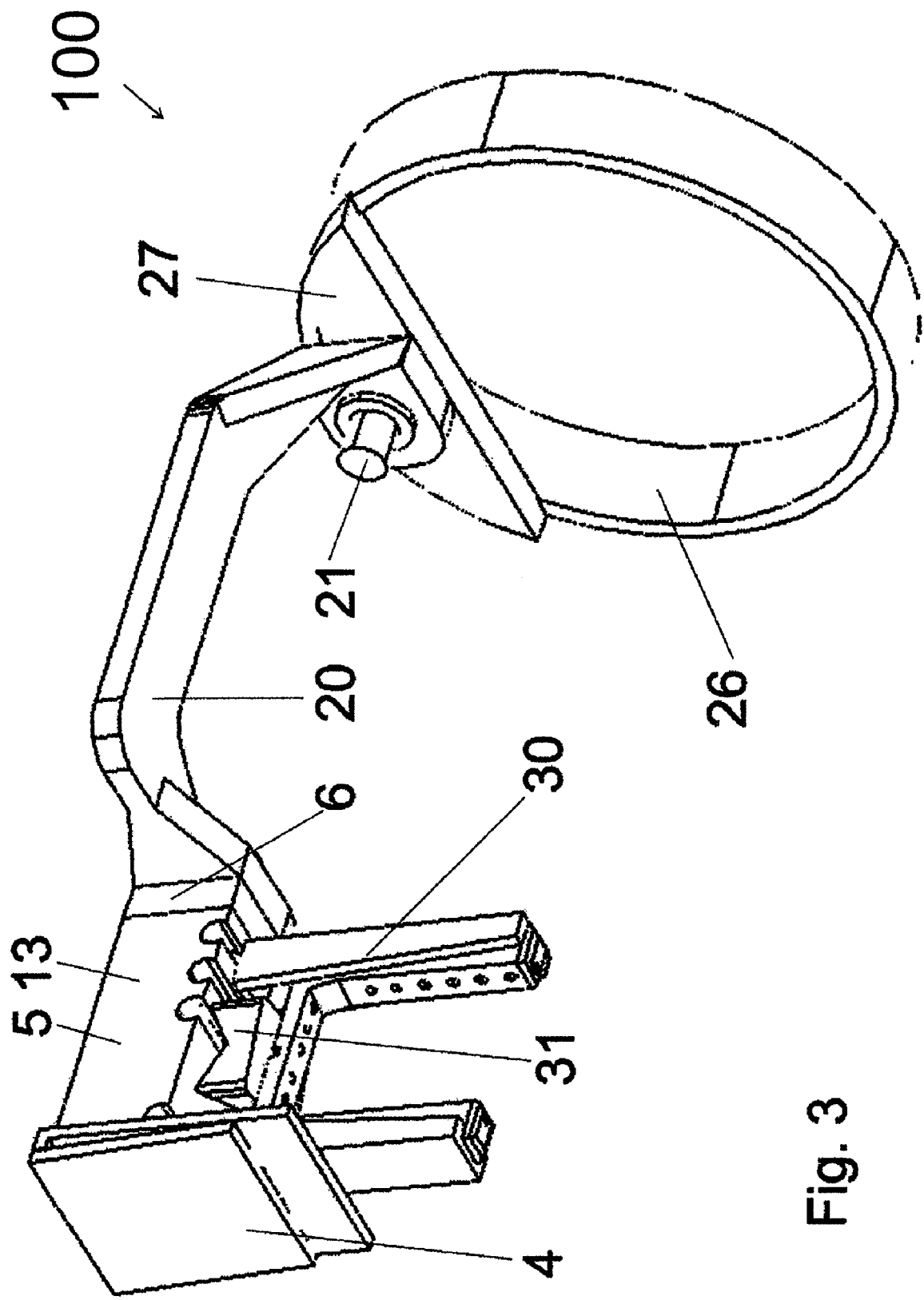

The present invention will now be described in greater detail with reference to an embodiment represented in the drawings. The figures show:

FIG. 1—an exploded perspective front view of the radiographic film positioning device of the present invention;

FIG. 2—an exploded perspective back view of the radiographic film positioning device of the present invention;

FIG. 3—a perspective front view of the radiographic film positioning device of the present invention, mounted.

DETAILED DESCRIPTION OF THE INVENTION

A dental implant is usually employed to recover the appearance of the mouth of a patient who has definitively lost one of more teeth.

As it is known, in addition to enabling mastication and chewing of foods in small portions (capable of going through the esophagus), the teeth have a number of important actuations, among which the esthetic appearance which they impart to people and still the influence which they exert on certain phonemes of speech, the pronunciation of which in the absence of the teeth are impaired. Therefore, the presence of teeth in the mouth is very important, from both the esthetic and functional point of view.

Typically, the procedure followed for a dental implant comprises using a synthetic tooth (technically referred to as prosthetic crown), which should be positioned at the site of the missing original tooth, for the purpose of restoring the capability of chewing and other properties attributed to the tooth.

A crown of tooth is fixed to an implant, which in turn is positioned inside an orifice made in the bone portion of the maxilla (upper arcade) or mandible (lower arcade) of the patient's mouth.

The implant should be correctly and steadily fixed to the bone, so that the prosthetic crown can be as stable as a natural tooth.

The perforation of the bone tissue for fixation of the implant must be made at a correct distance from the adjacent tooth, in order to guarantee the correct positioning of the prosthetic crown, in both aesthetic and functional aspect. Therefore, the bore must be such that it will enable correct anchorage of the implant on the bone. For this purpose, the professional should consider a number of other variables in order to determine the correct positioning of the implant, such as profile and relief of the bone portion at the implant site, positioning of the maxillary sinus, of the nasal cavity floor and of the lower alveolar nerve, among others.

Therefore, even though the question of positioning the orifice is quite delicate, it is common for the professional to make the orifice based on periapical radiographic images obtained with positioners that do not guarantee the necessary accuracy of the images. However, because of the limited space in the patient's mouth (which makes the work of the professional difficult), it is extremely troublesome and fallible to determine the correct positioning of the orifice and make it without preliminary studies based reliable images. Except rare cases, the site where the implant is positioned is away from the desired position, and one of the factors responsible for this inaccuracy are the radiographic images obtained without correct positioning between the radiographic film and the border of the alveolar bone of the patient, a situation in which they present deformations/distortions due to wrong alignment of the film with respect to the bone.

In the procedure of determining the position of implantation by using radiographic images, the professional first makes a plaster model of the patient's dental arcade and, based on it, he makes a plate of polymeric material (as a rule, acetate or thermoplastic PVC). This plate is widely known among the dentistry professionals, being easy to manufacture and having a very low cost.

A radiographic support 30 is installed on the plate, which can be seen in the figures and is an object of the Brazilian patent application, still without an official number, but with protocol number 020080078794, filed on May 25, 2008, in the name of the same applicants of the present application, the contents of which should be integrally incorporated into the present application.

Essentially, the radiographic support 30 comprises a body substantially in the shape of inverted U, defining a first main portion having two free ends, from each of which a respective prolonged orthogonal portion extends (which configure the 'legs' of the "U").

The first main portion and the two prolonged orthogonal portions define a space that will be occupied by the anatomic mandible or maxilla portion when the support is installed in the patient's mouth.

Describing the support 30 in greater detail, the first main portion comprises a first surface facing the space defined, and a second, opposite surface. Analogously, each of the prolonged orthogonal portions comprises a first surface facing the defined space and a second, opposed surface.

Preferably, the prolonged orthogonal projections have the same length and are substantially parallel to each other and substantially perpendicular with respect to the main portion, but it is evident that the geometric details may vary freely, all the more because the anatomy of the maxilla and of the mandible varies greatly from person to person.

The radiographic support 30 comprises a plurality of tubular through orifices to enable the transgingival probing, positioned in an inclined and strategic manner, so as to enable the probing at several points of the gum.

The support 30 further comprises, optionally, two radiopaque bodies that enable correct viewing of the support when making X-ray plates. The deformation of the image generated by radiography will lead to a deformation of the shape of the radiopaque body, which may be measured. In possession of the value of deformation of the radiopaque body, one can determine, in an inverse calculation, which the real bone measurements would be, in a sufficiently precise manner.

The radiographic film positioning device 100 of the present invention is associated with the support 30, which, as explained and proven in said Brazilian patent application with protocol number 020080078794, is positioned perfectly perpendicular to the alveolar bone of the mandible or maxilla. Evidently, the support 30 is may be positioned in a precise and secure manner, so that the positioning of the radiographic film can be successful.

Depending on the need for a surgical procedure, the support 30 may be positioned on the plaster model of the patient's dental arcade.

As can be seen in the figures, the radiographic positioner 100 comprises three portions or assemblies, namely: a first assembly 1 referring to the positioning of the radiographic film (plate), a second connection assembly 2 and a third assembly in the form of a rim 3 for radiographic orientation, both operatively associated with each other.

In essence, the first assembly 1 is responsible for positioning the radiographic film on the device 100 and for positioning the device 100 at the dental arcade of the patient, so that the film will be completely parallel to the alveolar bone.

In the preferred embodiment of the present invention, the film positioning assembly 1 is formed by a film support element 4, a main body 5, a connector 6 and at least one association means 7 for association to said radiographic support 30.

The film support element 4 may have any necessary or desirable shape, so that it can support the radiographic film (not shown) correctly, but preferably it comprises a first plate 8 and a second plate 9, the first plate being jointed at the top with a little apart from the second plate 9. The first plate 8 is slightly inclined with respect to the second plate 9, so that, in the region opposite that where the joining between them (a small spacing) takes place, they touch each other. When the radiographic film is positioned in the space between the plates 8, 9, the ends of the two plates that touch each other act as tweezers, preventing the film from moving and guaranteeing the positioning thereof with respect to the support element. The support element 4 further comprises an elongate shaft 10, for association with the main body 5, preferably of rectangular or square cross-section. The plate 9 is perfectly perpendicular to the shaft 5.

It should be noted that the shape and the functionality of the film support element 4 may vary freely, as long as it has the capability of retaining the radiographic film in place, without the invention failing to be included in the protection scope of the accompanying claims.

The main body 5 is the main structural component of the positioning assembly 1 and has any prismatic shape, but it should be preferably formed by a parallelepiped-shaped block 11, provided with a longitudinal through bore 12 having a cross-section cooperating with the elongate shaft 10 and by the fitting element 13. Preferably, two and more preferably four fitting grooves 13 are provided, preferably semicircular and through grooves, located in the face of the body 5 facing the dental arcade (in the figures, the lower face). The through bore 12 is perfectly in axial alignment with respect to the body 5.

In the preferred embodiment, there is a groove positioned adjacent the end of the body 5, which is adjacent the film support element and other three grooves, closer to each other, facing the opposite end of the body 5, which is also associated with said connector 6. However, it is evident that other solutions con be proposed, without the invention failing to be included in the protection scope of the accompanying claims.

The connector 6 is formed by a support plate 14, preferably square and rectangular, which defines two main opposite surfaces. From the first surface facing the main body 5, a fitting shaft 15 with cross-section cooperating with the longitudinal through bore 12 of the main body 5 extends. The second main surface, in turn, comprises a central recess 16 and a threaded central bore 17, preferably circular, both concentric. The fitting shaft 15 is preferably perpendicular to the support plate 14.

The association means for association to the radiographic support 30 have the preferred embodiment of fitting shaft 7, even though it is evident that they may vary.

Preferably, two analogous shafts 7 are provided, each having a substantially elongate shape, forming an elongate fitting channel 18, at one main end of which a fitting head 19 is provided, which cooperates with the fitting grooves 13 and, therefore, preferably transverse and semicircular. Preferably, the fitting head of each groove articulates inside in a single direction and to both sides in the fitting grooves 13. Further preferably, the shape of the grooves 13 and of the fitting heads 19 of the shafts is such that, although the pivotal motion is possible, the grooves 13 are prevented from easily disengaging from the fitting heads 19.

It is evident, therefore, that the variation in the shape of the fitting grooves 13 causes a corresponding variation in the shape of the fitting head 19 of each shaft 7, but anyway both may vary freely, without the invention failing to be included in the protection scope defined by the accompanying claims.

The shafts 7 have the function of fixing the device 1 to said support 30, which is achieved by cooperation of the elongate fitting channels 18 with the outer faces of the orthogonal projections of the support 30 (this can be clearly seen in FIGS. 1 to 3). The fitting channels 18 of the two shafts 7 involve the orthogonal projections of the support 30, consequently fixing the main body of to the support 30.

And, since the size of the support 30 may vary, it is possible to fix the shafts in one or another of the three channels 13 facing the end of the body 5, which is associable to said connector 6.

In order to fix the shafts to the support 30 correctly, it is enough to position a first shaft 7 in the single groove 13 located adjacent the film support element 4 and the second shaft 7 in one of the other grooves 13, and one should choose that which enable the shaft 7 associated with it to cooperate effectively with the support 30, that is to say, to allow it to be substantially perpendicular to the body 5 and parallel to the orthogonal projection of the support 30 to which it is associated.

The main body 5 is perfectly aligned with the support 30, by virtue of the tight-fitting association of the fitting channels 18 of the two shafts 7 with the respective orthogonal projections of the support.

Said connection assembly 2 is formed essentially by a connection shaft 20 having a first end associable to said connector 6 and a second end associated with a radiographic orientation rim 3, or the like, which will be described later.

Preferably, the shaft 20 is composed of a frame 23, the ends of which comprise a respective through bore 24, the back end further having a circular outer shoulder 25, although evidently its constitution may vary considerably, if necessary or desirable.

Further preferably, two manual tightening screws 21 (which fix the shaft to the connector 6 and to the rim 3) and a screw nut 22 with spacing and self-locking function.

Finally, said third assembly comprises said radiographic orientation rim 3, designed for enabling the correct positioning of the X-ray emitter with respect to the radiographic film, so that said X-rays will fall perpendicularly onto the radiographic film at the time of taking the radiographic picture. The radiographic rim is a component known by those skilled in the art and comprises an enclosing rim 26 associated with a support plate 27 provided with connection means for connection to said shaft 20. Preferably, these connection means comprise a circular shoulder 28 provided with a central threaded bore 29, to which one of said screws 21 can be threaded, fixing the shaft to the rim, so that the rim 3 will be substantially perpendicular to the shaft 20.

The other screw 21 is threaded to the bore 17 provided in the connector 6, fixing the shaft 20 to it.

Evidently, the enclosing rim 26 may assume any other necessary or desirable configuration, as well as the forms of fixing it may vary greatly, without the invention failing to be included in the protection scope defined by the accompanying claims.

Preferably, the radiographic positioner of the present invention is made from any radiolucent rigid material, preferably injectable acrylic, but evidently it may be made from any other necessary or desirable material, without the invention failing to be included in the production scope of the claims.

The preferred embodiment of the device 100, illustrated in FIGS. 1 to 3, is assembled as follows.

Initially, one assembles the assembly 1 by connecting the support 4, connector 6 and shafts 7 to the main body 5. As mentioned, the distance between the shafts 7 should be equivalent to the width of the radiographic support 30 to be used. The elongate fitting shafts 10 and 15, belonging to the support 4 and to the connector 6, respectively, are introduced into said longitudinal through bore 12 of the support 5, and the fitting heads 19 of the shafts are inserted into the fitting grooves 13 provided in the body 5.

The introduction of the elongate fitting shafts 10 and 15 of the longitudinal through bore 12 of the support 5 already guarantees the perfectly perpendicular positioning of the plate 9 and of the support plate 14 with respect to the body 5. In this way, the perpendicular positioning of the radiographic film with respect to the body 5, for example, with respect to the two shafts 7 is guaranteed, just as the aligned positioning of the rim 3 with respect to the body 5 is guaranteed (which will guarantee the perfect positioning of the X-ray emitter).

Since the shafts 7 have the function of fixing the device 1 to the support 30 (which is achieved by cooperation of the elongate fitting channels 18 with the end faces of the orthogonal projections of the support 30), and since the size of the support 30 may vary, one should fix a first shaft 7 to the single groove 13 positioned adjacent the film support element 4 and the second shaft 7 in one of the other three grooves 13, and one should choose that which enables the shaft 7 associated with it to cooperate effectively with the support 30, that is to say, to allow it to be substantially perpendicular to the body 5 and parallel to the orthogonal projection of the support 30 to which it is associated. The main body 5 remains perfectly aligned with the support 30, by virtue of the tight-fitting association of the fitting channels 18 of the two shafts 7 with the respective orthogonal projections of the support.

Then, one should fix the connection shaft 20 to the connector 6 by threading one of the screws 21 into the threaded bore 17. With the aid of the other screw 21 and of the nut 22, one also fixes the enclosing rim 26 to the connection shaft 20. Shaft and rim 20, 26 can be adjusted in rotation thanks to the cooperation of the circular shoulders 25, 28, but they are always in perfect alignment with the body 5.

Finally, the positioner 100 having been assembled, one should then put the radiographic film in the space between the two plates 8, 9 of the support 4, and it will be correctly positioned in place by virtue of the fact that the ends of the two plates touch each other, acting as tweezers. Thus, in the face of all that has been set forth above, when the device 100 is assembled, the positioning of the support element 4 substantially perpendicular to the former will be substantially guaranteed.

Once the positioner 100 has been assembled, the use thereof takes place in two steps.

Initially, one adjusts the assembly by using the plaster model of the dental arcade of the patient, the acrylic plate, which contains the radiographic support 30 being placed on it, will be fitted into said model.

Then, the assembly formed by the main body 5 and by the shafts 7 should be coupled to the support 30, until the lower face of the main body 5 touches a prosthetic crown 31, which is fixed to the support 30. One should then adjust the positioning of the connection shaft 20 parallel to the occlusion plane and of the rim 3, guaranteeing that the latter will be perfectly aligned and parallel to the support 4.

Finally, one positions the x-ray emitter of the equipment against the rim 26, which will guarantee the positioning thereof perfectly aligned with the various elements of the device 100 and, in the last analysis, perfectly aligned with the tissues of the patient and with the radiographic film.

Thus, one can make the radiographic images with a high degree of accuracy, without distortions and deformations, further enabling one to calculate the magnification.

A process for obtaining radiographic images by positioning the presently defined positioning device at the dental arcade of a patient is also a novel and creative invention, the single configuration of said positioner may be adjusted so as to obtain periapical radiographic images of the whole dental arcade of the patient. In essence, the process comprises the following steps:

(i) assembling the device 100;

(ii) positioning the device 100 with respect to the dental arcade;

(ii) positioning at least one X-ray emitting source with respect to the device 100; and (iv) actuating the X-ray emitting source.

A preferred embodiment having been described, one should understand that the scope of the present invention embraces other possible variations, being limited only by the contents of the accompanying claims, which include the possible equivalents.

The invention claimed is:

1. A radiographic film positioning device comprising a first assembly for positioning at least one radiographic film and for positioning said device over a radiographic support element having been positioned over a dental arcade of a patient, a second connection assembly and a third assembly for radiographic orientation, the second assembly connecting said first assembly to said third assembly, said first assembly comprising at least one association means for association of the device to the radiographic support element, wherein:

said device is positioned substantially perpendicular to a bone portion of the patient; and said association means comprises an elongated coupling shaft forming an elongated fitting channel.

2. A device according to claim 1, wherein said elongated coupling shaft comprises at one of its main ends a fitting head.

3. A device according to claim 1, further comprises a main body, wherein said radiographic support element, a said main body and said means for association are operatively associated.

4. A device according to claim 3, wherein said main body is formed by a parallelepiped-shaped block, provided with a longitudinal through bore having a cross section and a fitting element cooperating with said elongated coupling shaft, said fitting element in the form of at least one fitting groove.

5. A device according to claim 4, wherein at least two or four fitting grooves are provided.

6. A device according to claim 4, wherein said at least one fitting grooves is semicircular and through grooves.

7. A device according to claim 6, wherein said fitting grooves are located in a face of said main body facing said patient's dental arcade.

8. A device according to claim 4, wherein said through bore is in axial alignment with respect to said main body.

9. A device according to claim 3, wherein said means for association is formed by a support plate that defines two opposite main surfaces characterized in that a fitting shaft with a cross-section cooperating with the longitudinal through bore of said main body extends from said first main surface of said support plate.

10. A device according to claim 9, wherein said second main surface of said support plate comprises a central concentric recess and a threaded concentric central bore.

11. A device according to claim 1, wherein said second assembly comprises a connection shaft characterized by having two ends, each comprising a through bore, with one end comprising an outer circular shoulder.

12. A device according to claim 11, wherein said connection shaft is composed of a frame.

13. A device according to claim 11, wherein said second assembly further comprises two manually tightening screws which fix said connecting shaft to said first assembly on one end and to said third assembly on the opposite end and screw nuts with spacing and self-locking functionality.

14. A device according to claim 11, wherein said third assembly comprises a radiographic orientation rim which further comprises an enclosing rim and at least one association means for association to said connection shaft.

15. A device according to claim 14, wherein said association means comprises a circular shoulder comprising a threaded central bore.

* * * * *